(12) United States Patent
Fink et al.

(10) Patent No.: US 10,698,982 B2
(45) Date of Patent: Jun. 30, 2020

(54) DETERMINING CORRELATION BETWEEN MEDICAL SYMPTOMS AND ENVIRONMENTAL FACTORS

(71) Applicant: International Business Machines Corporation, Armonk, NY (US)

(72) Inventors: Patrick W. Fink, Charlotte, NC (US);
Kristin E. McNeil, Charlotte, NC (US);
Philip E. Parker, York, SC (US);
David B. Werts, Charlotte, NC (US)

(73) Assignee: International Business Machines Corporation, Armonk, NY (US)

( * ) Notice: Subject to any disclaimer, the term of this patent is extended or adjusted under 35 U.S.C. 154(b) by 1133 days.

(21) Appl. No.: 15/052,195

(22) Filed: Feb. 24, 2016

(65) Prior Publication Data
US 2017/0242970 A1    Aug. 24, 2017

(51) Int. Cl.
*G06F 19/00* (2018.01)
*G06F 16/35* (2019.01)

(52) U.S. Cl.
CPC .......... *G06F 19/3418* (2013.01); *G06F 16/35* (2019.01); *G06F 19/324* (2013.01)

(58) Field of Classification Search
CPC ............. G06F 19/3418; G06F 19/3481; G06F 19/324; G06F 19/322; G06F 16/35
USPC ........................................................ 705/2-3
See application file for complete search history.

(56) References Cited

U.S. PATENT DOCUMENTS

2010/0145720 A1    6/2010 Reiner
2010/0318424 A1 * 12/2010 LaValle ............... G06F 19/3418
                                                         705/14.58

2013/0332194 A1    12/2013 D'Auria et al.
2014/0118142 A1    5/2014 Narayanaswami
2014/0122122 A1    5/2014 Cooper et al.
(Continued)

FOREIGN PATENT DOCUMENTS

CA      2421220 A1    3/2002
WO   2005008555 A1    1/2005
(Continued)

OTHER PUBLICATIONS

Neustein, Amy, et al; "Application of text mining to biomedical knowledge extraction: analyzing clinical narratives and medical literature." De Gruyter, Berlin 50 (2014).
(Continued)

*Primary Examiner* — Joy Chng
(74) *Attorney, Agent, or Firm* — Joseph Polimeli; Edell, Shapiro & Finnan, LLC

(57) ABSTRACT

A method, a processing device, and a computer program product are provided. Unstructured text may be analyzed to identify medical condition information of multiple occurrences of a medical condition for at least one subject. Times and geographic locations corresponding to the multiple occurrences of the medical condition may be obtained. Environmental information that corresponds to the times and the geographic locations of the multiple medical condition occurrences, may be retrieved. Correlations between the medical condition information and the retrieved environmental information for the at least one subject may be determined. Environmental factors affecting the medical condition, based on the determined correlations, are identified.

14 Claims, 4 Drawing Sheets

(56) References Cited

U.S. PATENT DOCUMENTS

| | | |
|---|---|---|
| 2014/0195255 A1 | 7/2014 | Ghosh et al. |
| 2014/0266682 A1* | 9/2014 | Gettings ................ G08B 23/00 340/517 |
| 2014/0278513 A1* | 9/2014 | Prakash ............. G06Q 30/0601 705/2 |
| 2015/0269347 A1 | 9/2015 | Bhatt et al. |
| 2016/0026768 A1* | 1/2016 | Singh .................. G06F 19/3418 705/3 |

FOREIGN PATENT DOCUMENTS

| | | |
|---|---|---|
| WO | 2009087269 A1 | 7/2009 |
| WO | 2014059390 A2 | 4/2014 |
| WO | 2014085794 A1 | 6/2014 |

OTHER PUBLICATIONS

Riga, Marina, et al; "Investigating the relationship between social media content and real-time observations for urban air quality and public health." ACM, 2014, 7 pages.

Eichstaedt et al., "Psychological Language on Twitter Predicts County-Level Heart Disease Mortality", http://pss.sagepub.com/content/early/2015/01/20/0956797614557867, Psychological Science, Jan. 20, 2015, 11 pages.

* cited by examiner

DETERMINING CORRELATION BETWEEN MEDICAL SYMPTOMS AND ENVIRONMENTAL FACTORS

BACKGROUND

Present invention embodiments are related to systems and methods for correlating medical symptoms and environmental factors. In particular, present invention embodiments are related to performing text analysis on unstructured text, requesting and receiving environmental information, such as weather information, and correlating medical symptoms as mentioned in the unstructured text with weather information. However, no study had been performed using natural language processing and machine learning to determine whether there is an actual correlation between a number of symptoms of medical conditions and environmental conditions including, but not limited to, weather conditions with respect to an individual or a group of subjects.

Many people believe that weather and environmental factors affect various illnesses. For example, some people believe that rain causes their sinus pressure to increase or that an old knee injury becomes achy before it rains. In another example, some people believe that the weather or pollen count affects asthma. However, no study had been performed using natural language processing and machine learning to determine whether there is an actual correlation between a number of symptoms of medical conditions and environmental conditions including, but not limited to, weather conditions with respect to an individual or a group of subjects.

SUMMARY

According to embodiments of the present invention, a computer-implemented method, a processing device, and a computer program product are provided. Unstructured text that includes medical condition information may be analyzed to identify the medical condition information. Times and geographic locations, corresponding to occurrences of a medical condition with respect to at least one subject, may be obtained. Environmental information that corresponds to the times and geographic locations of the occurrences of the medical condition may be retrieved and correlations between the medical condition information and the environmental information, with respect to the at least one subject, may be determined. Based on the determined correlations, environmental factors affecting the medical condition may be identified.

The term "time" as used throughout this specification is defined to include a time of day and/or a date. The term "times" as used throughout this specification is defined to include times of day and/or corresponding dates.

BRIEF DESCRIPTION OF THE DRAWINGS

Generally, like reference numerals in the various figures are utilized to designate like components.

DETAILED DESCRIPTION

Figure 1:
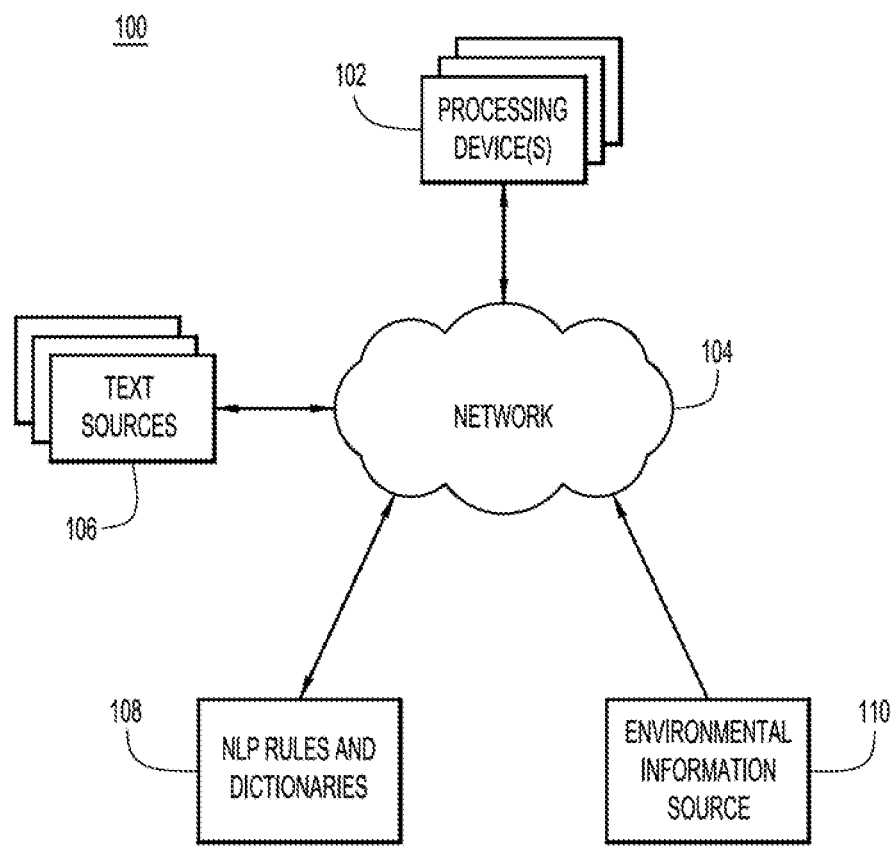
FIG. 1 illustrates an example environment in which embodiments may be implemented.

With reference now to FIG. 1, an example environment 100 for implementation of embodiments is shown. One or more processing devices 102 may receive input from text sources 106, either directly or via a network 104. The text sources may include, but not be limited to, email, social media messages, doctors' notes, and medical records. The one or more processing devices 102 may analyze text input from text sources 106 using natural language processing rules and dictionaries 108. One or more processing devices 102 may receive environmental information from third party environmental information source 110. The environmental information may include weather information for an area at a particular time as may be indicated in the text input. One or more processing devices 102 may produce output indicating whether a correlation exists between various medical symptoms and environmental factors and a strength of the correlation. The environmental factors may include, but not be limited to, weather information.

Network 106 may be implemented by any number of any suitable communications media (e.g., wide area network (WAN), local area network (LAN), Internet, Intranet, etc.). In some embodiments, one or more processing devices 102 and natural language processing rules and dictionaries 108 may be local to each other and may communicate via any appropriate local communication medium (e.g., local area network (LAN), hardwire, wireless link, Intranet, etc.).

Figure 2:
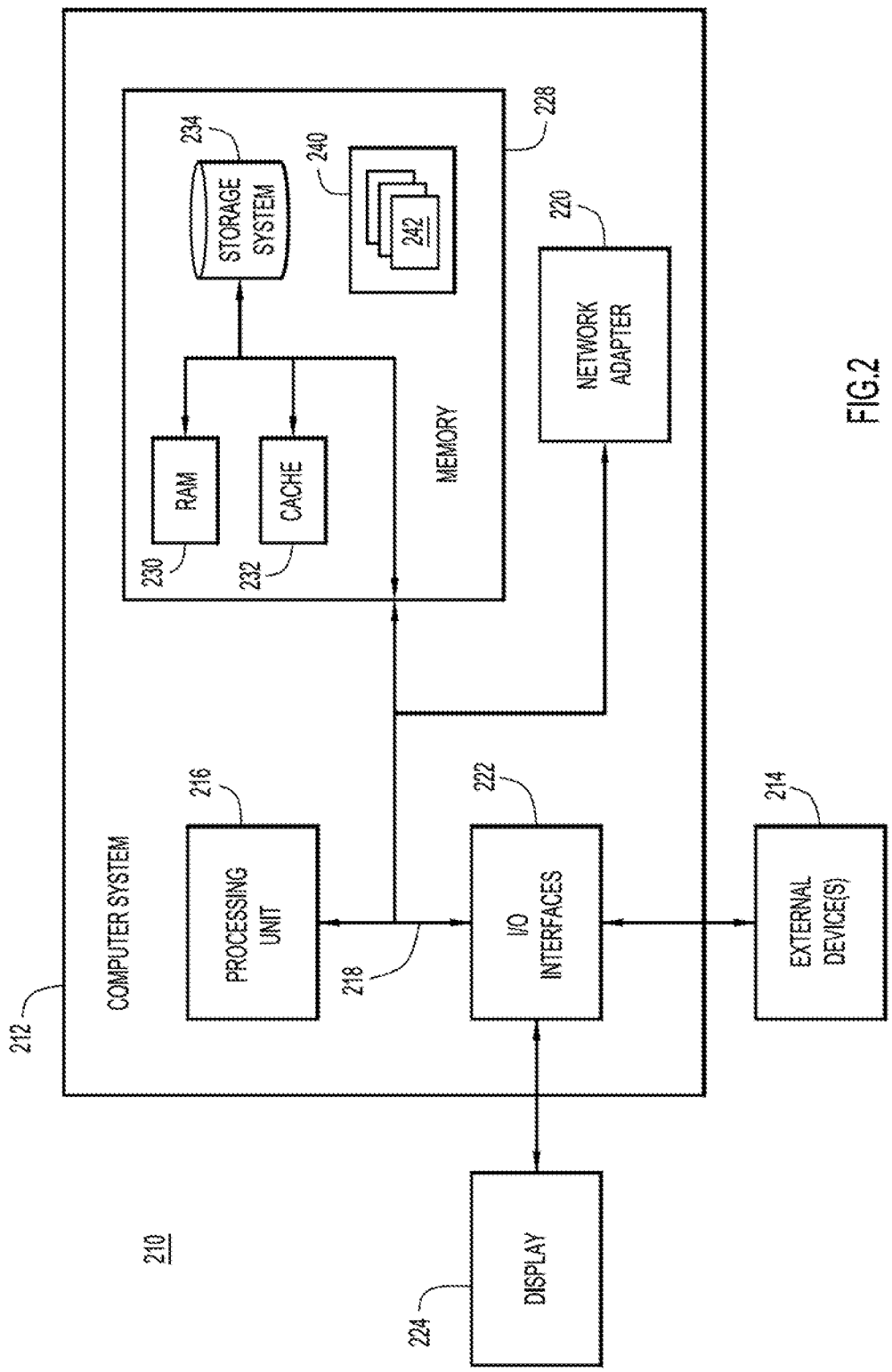
FIG. 2 illustrates an example of a processing device capable of performing functions of various embodiments.

Referring now to FIG. 2, a schematic of an example processing device 210 is shown, which may implement a processing device of one or more processing devices 102. Processing device 210 is only one example of a suitable processing device for the environment of FIG. 1 and is not intended to suggest any limitation as to the scope of use or functionality of embodiments of the invention described herein. Regardless, processing device 210 is capable of being implemented and/or performing any of the functionality set forth herein.

In processing device 210, there is a computer system 212 which is operational with numerous other general purpose or special purpose computing system environments or configurations. Examples of well-known computing systems, environments, and/or configurations that may be suitable for use with computer system 212 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system 212 may be described in the general context of computer system executable instructions, such as program modules, being executed by a computer system. Generally, program modules may include routines, programs, objects, components, logic, data structures, and so on that perform particular tasks or implement particular abstract data types. Computer system 212 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 2, computer system 212 is shown in the form of a general-purpose computing device. Components of computer system 212 may include, but are not limited to, one or more processors or processing units 216, a system memory 228, and a bus 218 that couples various system components including system memory 228 to one or more processors 216.

Bus 218 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system 212 typically includes a variety of computer system readable media. Such media may be any available media that is accessible by computer system 212, and includes both volatile and non-volatile media, removable and non-removable media.

System memory 228 can include computer system readable media in the form of volatile memory, such as random access memory (RAM) 230 and/or cache memory 232. Computer system 212 may further include other removable/non-removable, volatile/non-volatile computer system storage media. By way of example only, storage system 234 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 218 by one or more data media interfaces. As will be further depicted and described below, memory 228 may include at least one program product having a set (e.g., at least one) of program modules that are configured to carry out the functions of embodiments of the invention.

Program/utility 240, having a set (at least one) of program modules 242, may be stored in memory 228 by way of example, and not limitation, as well as an operating system, one or more application programs, other program modules, and program data. Each of the operating system, the one or more application programs, the other program modules, and program data or some combination thereof, may include an implementation of a networking environment. Program modules 242 generally carry out the functions and/or methodologies of embodiments of the invention as described herein.

Computer system 212 may also communicate with one or more external devices 214 such as a keyboard, a pointing device, a display 224, etc.; one or more devices that enable a user to interact with computer system 212; and/or any devices (e.g., network card, modem, etc.) that enable computer system 212 to communicate with one or more other computing devices. Such communication can occur via Input/Output (I/O) interfaces 222. Still yet, computer system 212 can communicate with one or more networks such as a local area network (LAN), a general wide area network (WAN), and/or a public network (e.g., the Internet) via network adapter 220. As depicted, network adapter 220 communicates with the other components of computer system 212 via bus 218. It should be understood that, although not shown, other hardware and/or software components could be used in conjunction with computer system 212. Examples, include, but are not limited to: microcode, device drivers, redundant processing units, external disk drive arrays, RAID systems, tape drives, and data archival storage systems, etc.

Figure 3:
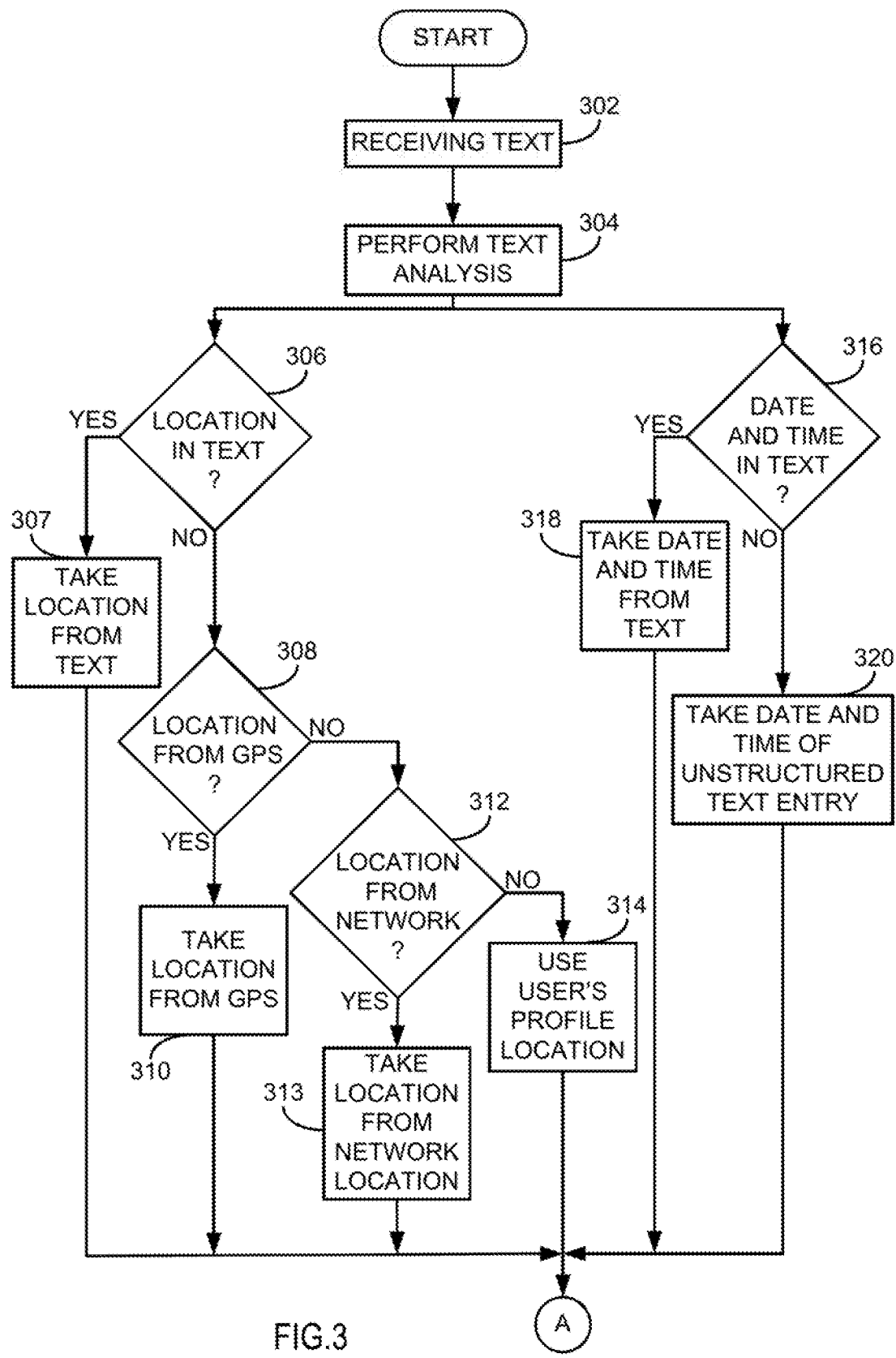
FIGS. 3-4 are flowcharts that illustrate example processing that may be performed in embodiments.
Figure 4:
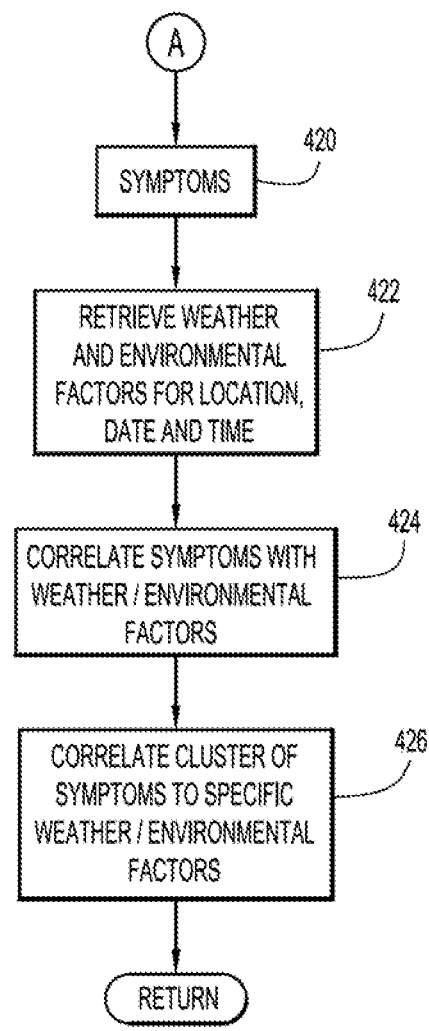

FIGS. 3 and 4 are flowcharts of an example process, which may be performed in various embodiments. The process may begin with receiving text (act 302). The text may be received from a number of sources including, but not limited to, emails, doctors notes, mobile applications and social media including, but not limited to, Facebook and Twitter. Natural language processing, including text analytics, may then be performed on the received text (act 304). The text analytics may use one or more predefined dictionaries and rules that identify medical symptoms, degree of symptoms, dates and location. The dictionaries and the rules are annotators and the result after analyzing the text are annotations.

One industry standard for context analytics is Unstructured Information Management Architecture (UIMA). UIMA is a component architecture and software framework implementation for the analysis of unstructured content such as text, video and audio data. UIMA includes software systems for analyzing large volumes of unstructured information in order to discover knowledge that is relevant to an end user. For example, a UIMA application may process text and identify entities, such as persons, places, organizations, or relations such as works-for or located-at. A UIMA pipeline is a list of individual stages, or Annotators, which are run serially. When a document is processed by the UIMA pipeline, a first annotator stage may create annotations covering sections of text. When the first stage is completed, the second annotator stage may then process the text. Each subsequent stage may read annotations created by earlier stages and may add or modify the annotations, thus building up a more complex analysis of contents of the document. The annotations could be for an entire document, a paragraph or sentence, a token or an annotation that one can define by creating a custom dictionary or a parsing rule including, but not limited to, a city, a disease, or a date of birth.

Another product for context analysis is IBM Advanced Care Insights from International Business Machines of Armonk, N.Y. IBM Advanced Care Insights has dictionaries for identifying various medical conditions and symptoms. Further, one may define custom dictionaries and rules for use with various embodiments. Some examples of custom dictionaries may include a date dictionary having words including, but not limited to, today, yesterday, January, February, March, etc. An example symptom dictionary may have words including, but not limited to, headache, pain, anxiety, bleeding, and swollen. An example environmental factors dictionary may have words or phrases including, but not limited to, pollen count, pollution, air quality, rain, sleet, snow, humid, and dry. An example rule may be as follows, where a token is a span of text:

<Date> <tokens> <Symptom>
<Symptom> <tokens> <Date>

Conventional machine learning techniques may be employed in a correlation module engine in order to correlate symptoms of a user with environmental factors including, but not limited to, weather conditions, which may be provided by a third-party.

Returning to the flowchart of FIG. 3, various embodiments may attempt to extract a location from the received text. If the location exists in the received text (act 306), then embodiments may take the location from the text (act 307). If the location does not exist in the text, then a check will be made to determine whether the location can be obtained from a GPS device (act 308). If the location can be obtained from the GPS device, then embodiments may take the location from the GPS device (act 310). Otherwise, embodiments may check for a network location (act 312). If there is a network location, then embodiments may take the location from the network location (act 313). Otherwise, embodiments may use the location from a user's predefined profile (act 314).

Similarly, embodiments may attempt to obtain a date and time from the text. If the date and the time exist in the received text (act 316) then embodiments may take the date and the time from the text (act 318). Otherwise, embodiments may take the date and time of an unstructured text entry of the received text (act 320).

Embodiments may obtain symptoms as well as a level of symptoms from the received text (act 420; FIG. 4). Environmental factors, which may include weather conditions, may be retrieved with respect to the obtained location and the obtained date and time (act 422). Conventional machine learning techniques may be employed to correlate symptoms with the environmental factors including, but not limited to, weather conditions (act 424). The machine learning techniques may attempt to find patterns in the data when correlating. Techniques such as clustering of like symptoms from multiple individuals may be performed to determine a relationship between a level of the like symptoms and the environmental factors (act 426). Various embodiments may produce a report indicating results of correlating the symptoms with the environmental factors.

After determining correlations between symptoms of medical conditions and environmental conditions, embodiments of the invention may monitor environmental conditions. When conditions are discovered that are correlated with aggravating symptoms of various medical conditions, embodiments may contact subjects suffering from the various medical conditions to alert them that current weather or environmental conditions may affect their particular symptoms and that they should take their medication or seek advice from their respective physicians. In an alternate embodiment, instead of contacting the various subjects, physicians of the subjects may be contacted so that the physicians may advise their patients regarding how to alleviate their symptoms.

In another embodiment, after determining correlations between symptoms of medical conditions and environmental conditions, embodiments of the invention may monitor environmental forecasts, including, but not limited to weather forecasts. Subjects or their physicians may be contacted when environmental forecasts or weather forecasts include conditions that are known to be correlated with affecting various symptoms of medical conditions.

The environment of the present invention embodiments may include any number of computer or other processing systems (e.g., client or end-user systems, server systems, etc.) and databases or other repositories arranged in any desired fashion, where the present invention embodiments may be applied to any desired type of computing environment (e.g., cloud computing, client-server, network computing, mainframe, stand-alone systems, etc.). The computer or other processing systems employed by the present invention embodiments may be implemented by any number of any personal or other type of computer or processing system (e.g., desktop, laptop, PDA, mobile devices, etc.), and may include any commercially available operating system and any combination of commercially available and custom software (e.g., browser software, communications software, server software, etc.). These systems may include any types of monitors and input devices (e.g., keyboard, mouse, voice recognition, etc.) to enter and/or view information.

It is to be understood that the software of the present invention embodiments may be implemented in any desired computer language and could be developed by one of ordinary skill in the computer arts based on the functional descriptions contained in the specification and flowcharts illustrated in the drawings. Further, any references herein of software performing various functions generally refer to computer systems or processors performing those functions under software control. The computer systems of the present invention embodiments may alternatively be implemented by any type of hardware and/or other processing circuitry.

The various functions of the computer or other processing systems may be distributed in any manner among any number of software and/or hardware modules or units, processing or computer systems and/or circuitry, where the computer or processing systems may be disposed locally or remotely of each other and may communicate via any suitable communications medium (e.g., LAN, WAN, Intranet, Internet, hardwired, modem connection, wireless, etc.). For example, the functions of the present invention embodiments may be distributed in any manner among the various systems, and/or any other intermediary processing devices. The software and/or algorithms described above and illustrated in the flowcharts may be modified in any manner that accomplishes the functions described herein. In addition, the functions in the flowcharts or description may be performed in any order that accomplishes a desired operation.

The software of the present invention embodiments may be available on a non-transitory computer useable medium (e.g., magnetic or optical mediums, magneto-optic mediums, floppy diskettes, CD-ROM, DVD, memory devices, etc.) of a stationary or portable program product apparatus or device for use with stand-alone systems or systems connected by a network or other communications medium.

The communication network may be implemented by any number of any type of communications network (e.g., LAN, WAN, Internet, Intranet, VPN, etc.). The computer or other processing systems of the present invention embodiments may include any conventional or other communications devices to communicate over the network via any conventional or other protocols. The computer or other processing systems may utilize any type of connection (e.g., wired, wireless, etc.) for access to the network. Local communication media may be implemented by any suitable communication media (e.g., local area network (LAN), hardwire, wireless link, Intranet, etc.).

The system may employ any number of any conventional or other databases, data stores or storage structures (e.g., files, databases, data structures, data or other repositories, etc.) to store information. The database system may be implemented by any number of any conventional or other databases, data stores or storage structures (e.g., files, databases, data structures, data or other repositories, etc.) to store information. The database system may be included within or coupled to a server and/or client systems. The database systems and/or storage structures may be remote from or local to the computer or other processing systems, and may store any desired data.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises", "comprising", "includes", "including", "has", "have", "having", "with" and the like, when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiments were chosen and described in order to best explain the principles of the invention and the practical application, and to enable others of ordinary skill in the art to understand the invention for various embodiments with various modifications as are suited to the particular use contemplated.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

We claim as our invention:

1. A computer-implemented method for identifying factors affecting a medical condition, the method comprising:
   analyzing unstructured text to identify medical condition information of a plurality of occurrences of the medical condition for at least one subject, the analyzing further comprising:
      creating, by a first stage of an annotator executing on a computing device, annotations covering sections of the unstructured text, and
      performing by subsequent stages of the annotator:
         reading annotations created by earlier stages of the annotator, and
         performing at least one from a group of adding to and modifying the annotations created by the earlier stages of the annotator, wherein
         the annotator includes one or more predefined dictionaries and rules that identify medical symptoms, degree of the medical symptoms, dates and a location;
   obtaining times and geographic locations corresponding to the plurality of occurrences of the medical condition, the times being obtained from one of a group of the contents of the unstructured text and a date and a time of an unstructured text entry of the unstructured text, and the geographic locations being obtained from one of a group of the contents of the unstructured text, a geographic location of a provider of the unstructured text supplied by a global positioning system device, a network location, and a corresponding user profile;
   retrieving environmental information corresponding to the times and the geographic locations of the occurrences of the medical condition;
   determining, via machine learning executing on the computing device, correlations between the medical condition information and the retrieved environmental information for the at least one subject;
   identifying environmental factors affecting the medical condition based on the determined correlations; and
   when the identified environmental factors that are correlated with aggravating symptoms of the medical condition are discovered, performing, by the computing device, at least one action including at least one from a group of alerting the at least one subject suffering from the medical condition to take medication and contacting a respective physician of the at least one subject.

2. The computer-implemented method of claim 1, wherein the unstructured text is from at least one of a group of social media, email, and medical documents.

3. The computer-implemented method of claim 1, wherein the environmental information includes weather information.

4. The computer-implemented method of claim 3, wherein the identifying environmental factors comprises:
   identifying weather conditions affecting the medical condition based on the determined correlations.

5. The computer-implemented method of claim 1, wherein the determining correlations comprises:
   determining correlations between medical condition information and retrieved environmental information aggregated for a plurality of subjects.

6. A computer program product comprising:
   one or more computer readable storage media collectively having computer readable program code embodied therewith for execution on a processing system, the computer readable program code being configured to be executed by the processing system to:
   analyze unstructured text to identify medical condition information of a plurality of occurrences of a medical condition for at least one subject, the analyzing further comprising:
      create, by a first stage of an annotator executing on a computing device, annotations covering sections of the unstructured text, and
      perform by subsequent stages of the annotator:
         reading annotations created by earlier stages of the annotator, and
         performing at least one from a group of adding to and modifying the annotations created by the earlier stages of the annotator, wherein
         the annotator includes one or more predefined dictionaries and rules that identify medical symptoms, degree of the medical symptoms, dates and a location;
   obtain times and geographic locations corresponding to the plurality of occurrences of the medical condition, the times being obtained from one of a group of the contents of the unstructured text and a date and a time of an unstructured text entry of the unstructured text, and the geographic locations being obtained from one of a group of the contents of the unstructured text, a geographic location of a provider of the unstructured text supplied by a global positioning system device, a network location, and a corresponding user profile;
   retrieve environmental information corresponding to the times and the geographic locations of the occurrences of the medical condition;
   determine, via machine learning executing on the processing system, correlations between the medical condition information and the retrieved environmental information for the at least one subject;
   identify environmental factors affecting the medical condition based on the determined correlations; and when the identified environmental factors that are correlated with aggravating symptoms of the medical condition are discovered, performing, by the computing device, at least one action including at least one from a group of alerting the at least one subject suffering from the medical condition to take medication and contacting a respective physician of the at least one subject.

7. The computer program product of claim 6, wherein the unstructured text is from at least one of a group of social media, email, and medical documents.

8. The computer program product of claim 6, wherein the environmental information includes weather information.

9. The computer program product of claim 8, wherein the identify environmental factors comprises:
identify weather conditions affecting the medical condition based on the determined correlations.

10. A processing device comprising:
at least one processor;
a memory; and
a communication bus connecting the at least one processor with the memory, wherein the memory has stored therein instructions, which when executed by the at least one processor cause the processing device to perform a method comprising:
analyzing unstructured text to identify medical condition information of a plurality of occurrences of a medical condition for at least one subject, the analyzing further comprising:
create, by a first stage of an annotator, annotations covering sections of the unstructured text, and
perform by subsequent stages of the annotator:
reading annotations created by earlier stages of the annotator, and
performing at least one from a group of adding to and modifying the annotations created by the earlier stages of the annotator, wherein
the annotator includes one or more predefined dictionaries and rules that identify medical symptoms, degree of the medical symptoms, dates and a location;
obtaining times and geographic locations corresponding to the plurality of occurrences of the medical condition, the times being obtained from one of a group of the contents of the unstructured text and a date and a time of an unstructured text entry of the unstructured text, and the geographic locations being obtained from one of a group of the contents of the unstructured text, a geographic location of a provider of the unstructured text supplied by a global positioning system device, a network location, and a corresponding user profile;
retrieving environmental information corresponding to the times and the geographic locations of the occurrences of the medical condition;
determining, via machine learning, correlations between the medical condition information and the retrieved environmental information for the at least one subject; and
identifying environmental factors affecting the medical condition based on the determined correlations; and
when the identified environmental factors that are correlated with aggravating symptoms of the medical condition are discovered, performing at least one action including at least one from a group of alerting the at least one subject suffering from the medical condition to take medication and contacting a respective physician of the at least one subject.

11. The processing device of claim 10, wherein the unstructured text is from at least one of a group of social media, email, and medical documents.

12. The processing device of claim 10, wherein the environmental information includes weather information.

13. The processing device of claim 12, wherein identifying environmental factors comprises:
identifying weather conditions affecting the medical condition based on the determined correlations.

14. The processing device of claim 10, wherein the determining correlations comprises:
determining correlations between medical condition information and retrieved environmental information aggregated for a plurality of subjects.

\* \* \* \* \*